United States Patent [19]

Deuter et al.

[11] Patent Number: 5,282,469
[45] Date of Patent: Feb. 1, 1994

[54] APPARATUS FOR MEASURING THE HEART WALL MOVEMENT OF A PERSON

[75] Inventors: Klaus Deuter, Freising; Jochen Körner, Munich, both of Fed. Rep. of Germany

[73] Assignee: Lre Relais and Elektronik GmbH, Munich, Fed. Rep. of Germany

[21] Appl. No.: 976,466

[22] Filed: Nov. 16, 1992

[30] Foreign Application Priority Data

Nov. 18, 1991 [DE] Fed. Rep. of Germany ....... 4137951
Aug. 28, 1992 [DE] Fed. Rep. of Germany ....... 4228766

[51] Int. Cl.⁵ ............................................. A61B 5/042
[52] U.S. Cl. ..................................... 128/644; 128/774
[58] Field of Search ................... 128/639–641, 128/643–644, 691, 694, 714, 774–775, 778, 781–782, 802

[56] References Cited

U.S. PATENT DOCUMENTS

| | | | |
|---|---|---|---|
| 4,559,953 | 12/1985 | Wright et al. | 128/680 |
| 4,646,747 | 3/1987 | Lundback | 128/802 X |
| 4,974,593 | 12/1990 | Ng | 128/644 X |
| 5,183,050 | 2/1993 | Kawamura | 128/672 X |

Primary Examiner—Angela D. Sykes

[57] ABSTRACT

In an apparatus for measuring the heart wall movement of a person, including a measuring head (10, 12) placeable on the breast with an electrode arrangement (76, 78) and a measuring circuit (84) for capacitively measuring the skin movement with respect to the electrode arrangement (76, 78), the measuring head has a holding ring (10) with an annular surface perpendicular to the ring axis (26) intended for placement on the body (30, 32) and straps for fastening the measuring head (10, 12) to the body. In the holding ring (10) is an adapter (12) including the electrode arrangement (76, 78) resiliently supported for movement in the direction of the ring axis (26) as well as in two other axes perpendicular to the ring axis and to one another. In one exemplary embodiment, the adapter (12) has an annular contact surface (42) intended for placement on a body and an electrode carrier (56) surrounded by the contact surface with a concave electrode carrying surface (74) in the center of which is formed an elevation (80) with at least one electrode (76, 78) being arranged in the annular section of the carrying surface (74) between the contact surface (42) and the elevation (80).

24 Claims, 4 Drawing Sheets

APPARATUS FOR MEASURING THE HEART WALL MOVEMENT OF A PERSON

FIELD OF THE INVENTION

The invention concerns an apparatus for measuring the heart wall movement of a person including a measuring head placeable on the breast and having an electrode arrangement with a measuring circuit for capacitively measuring the skin movement relative to the electrode arrangement.

BACKGROUND OF THE INVENTION

An apparatus of the previously mentioned kind serves to create a so-called cardiokymogram (CKG) which especially in combination with an electrocardiogram (EKG) can provide information as to whether the heart muscle upon stimulation by impulses visible in the EKG contracts in an orderly way. The heart wall movement continues to the tissue and can be detected on the outer surface of the breast as a very small movement of the skin. This movement can for example be detected if the outer surface of the skin and an electrode form a condenser contained in the frequency determining portion of an oscillator. One such movement of the skin causes a change in the capacity of such condenser and thereby a change in the oscillation frequency of the oscillator. The thereby evoked frequency modulation permits the production of a signal representing the heart wall movement.

The movement to be captured has a very small amplitude and is therefore not only influenced by the properties of the tissue and of the skin, but is also superimposed on body movements produced by breathing or otherwise. With a previously known apparatus of the aforementioned kind, it was possible to obtain usable signals only under laboratory conditions and through absolute quieting of the patient to be examined. With this, however, it was not previously possible to create a CKG with simultaneous stressing of the patient's body. Basically heart flaws can usually first be discovered with body stressing of the patient. For this, portable measuring devices have already been made which make possible the obtainment of a 24 hour EKG. The parallel taking of a CKG over the same amount of time was not possible with the previously known measuring apparatus.

SUMMARY OF THE INVENTION

The invention has as its object the provision of an apparatus of the aforementioned kind which can be carried by the body of the examined person and which is largely insensitive to disturbing influences created by the breath or other movement of the examined person.

This object is solved in accordance with the invention in that the measuring head includes a holding ring having an annular surface perpendicular to the ring axis intended for engagement with a body and means for fastening the measuring head to a body, in that in the holding ring is an adapter which contains the electrode arrangement and which adapter is resiliently movably supported for movement in the direction of the ring axis as well as in two axes perpendicular to the ring axis and to one another, and in that the adapter has an annular contact surface intended for engagement with the body and an electrode carrier surrounded by the support surface with at least one electrode carrying surface which is perpendicularly spaced relative to the support surface and is provided with a spacing element.

With the help of the holding ring the measuring head can be undisturbably fixed to the body of the person. The fastening can for example take place by means of breast and shoulder straps holding the holding ring. Since the adapter is resiliently movable relative to the holding ring and is supported quasi-cardonically by the holding ring, it can suit its position to the body shape in the measurement region and is moreover independent of the pressure at which the holding ring is pressed against the body, it being pressed alone against the body by the pre-given spring force. This makes it possible on one hand to so attach the measuring head to a body that it is not shifted by the usual body movements and on the other hand to maintain a spacing in the desired area between the skin and the electrode which deliver a measuring signal. The spacing element assures a relatively large surfaced measuring area by maintaining a nearly constant spacing between skin and the electrode outer surface within the measuring surface.

Since the firmness of the skin and of the underlying tissue of examined persons can differ widely, it is helpful if the spacing between the electrode and skin can be individually adjusted after the placement of the measuring head. With regard to this, it is therefore provided that the electrode carrier is adjustable relative to the contact surface in the direction of the ring axis, that is essentially perpendicularly to the outer surface of the body. Preferably, the adapter has a cup-shaped housing on the opening edge of which the contact surface is formed, while the electrode carrier together with the measuring circuit is arranged inside of the housing. In this case, the adjustment can take place in a simple way in that the electrode carrier is pretensioned by spring means in the direction toward the cup or housing bottom and is movable away from the housing bottom by an adjustment device. In a simple to make and to operate embodiment, the housing bottom is rotatable about the ring axis relative to the housing wall and carries on its inner side at least one cam which cooperates with a control surface on the electrode carrier which is inclined with respect to an axis normal plane. By the rotation of the housing bottom, through the inclined, for example ramp-shaped, control surface on the electrode carrier, the electrode carrier is adjusted in the axial direction.

The connection of the person's skin which forms the second condenser electrode to the measuring circuit takes place in a simple case in that the annular contact surface of the adapter is electrically conducting, the housing wall of the adapter housing for example being made of metal.

A substantial increase in the reliability of the measuring head of the invention can be achieved if two electrodes are provided which are, for example, of annular shape and arranged concentrically to one another on the carrier surface and about the central elevation, with each of these electrodes being arranged in an oscillator of the measuring arrangement. The evaluation of the measuring signals can therefore take place in that each oscillator delivers half of the signals. When one of the electrodes becomes short-circuited, because the skin rests on the electrode and therefore the involved oscillator cannot deliver a measurement signal, the other oscillator at least makes possible the carrying forward of the measurement.

Alternatively to this, both electrodes can be connected to a single oscillator so that each individual capacity determines the duration of a half wave of the output signal. In this embodiment also, the measurement can be carried forward if one electrode engages the skin.

Further features and advantages of the invention will be apparent from the following description, which in combination with the accompanying figures explain the invention by means of exemplary embodiments.

DETAILED DESCRIPTION OF THE PREFERRED EMBODIMENTS

Figure 1:
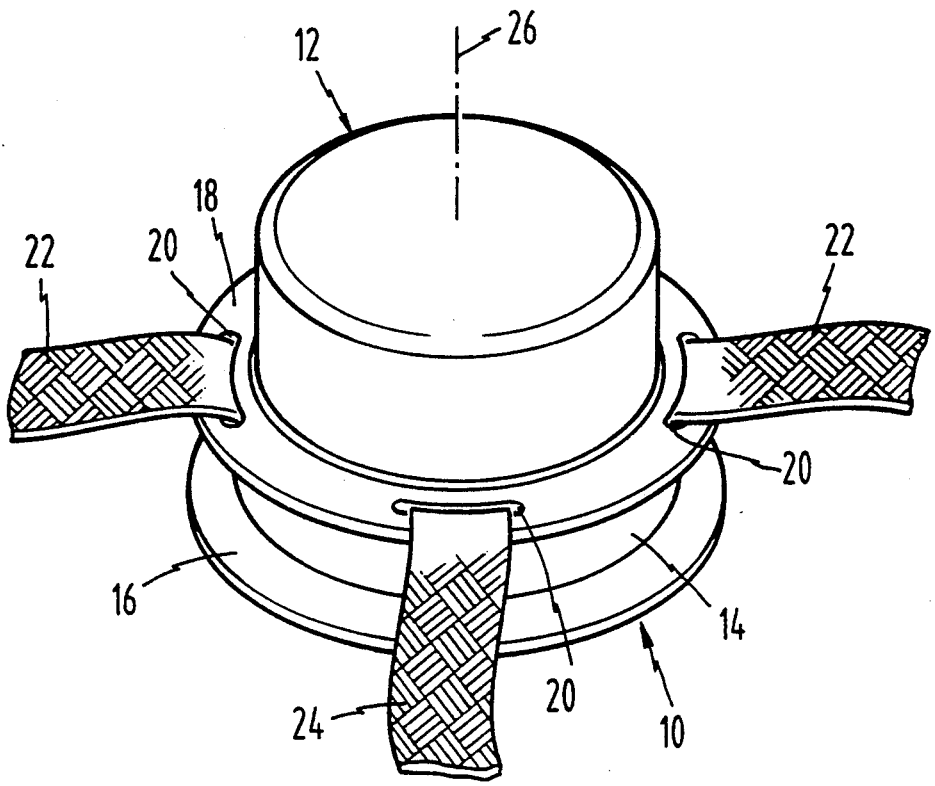
FIG. 1 A simplified perspective view illustrating the measuring head.
Figure 2:
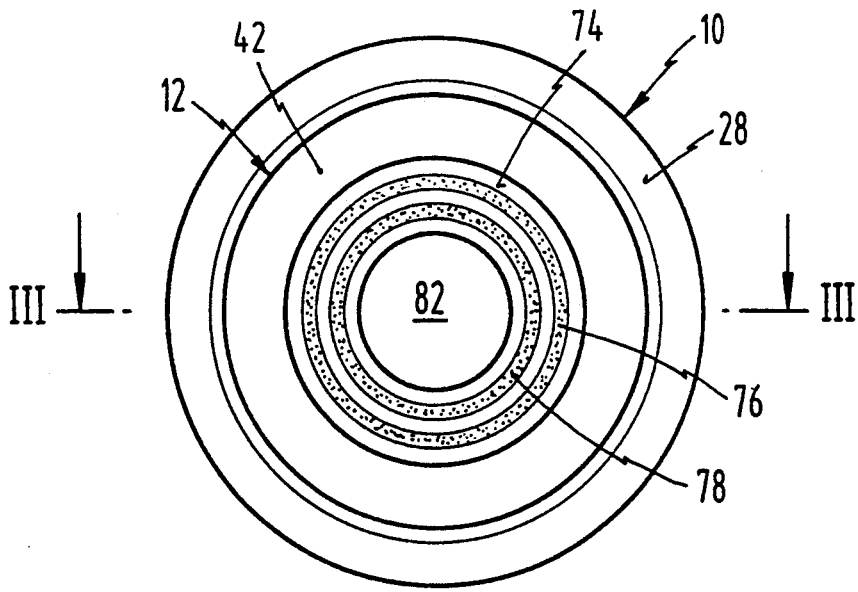
FIG. 2 A plan view of the forward side of the measuring head which faces the person during a measurement, FIG. 3 A sectional view containing the axis of the measuring head embodying the invention and taken along the line III—III in FIG. 2 with the measuring head being illustrated in its body engaging position, FIG. 4 A plan view of a spring between the adapter and the holding ring, FIG. 5 A side view of the spring illustrated in FIG. 4, FIG. 6 A schematic illustration of the measuring principle, FIG. 7 An illustration of a further exemplary embodiment with a flat electrode carrying surface, and FIG. 8 A plan view of the elastic suspension of the exemplary embodiment of FIG. 7.
Figure 3:
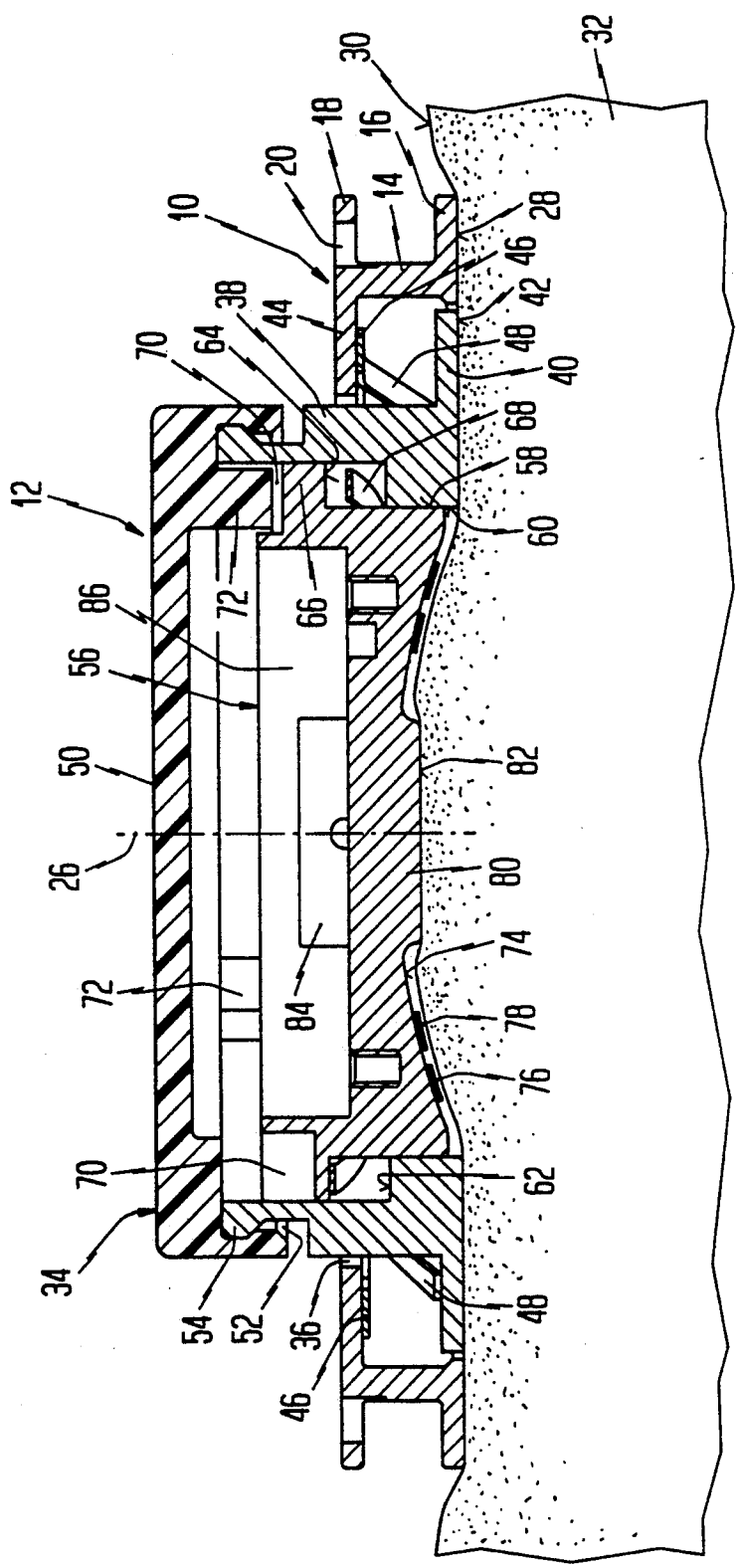

The measuring head illustrated in FIG. 1 includes a holding ring indicated generally at 10 and an adapter 12 movably supported in and circumferentially surrounded by the holding ring, which adapter 12 contains the actual measuring apparatus. The holding ring 10 includes a cylindrical wall 14 with a first radially outwardly directed flange 16 and a second radially outwardly directed flange 18. Slots 20 are formed in the latter flange 18 to which a breast strap 22 and a shoulder strap 24, illustrated only partially in FIG. 1, are fastened, and by means of which straps the measuring head can be undisturbably fixed to the breast of a patient. Thereby the holding ring 10 lies on the skin 30 (FIG. 3) of the person with an annular surface 28 directed perpendicularly to its axis 26 and is pressed into the skin more or less deeply by the tension of the straps 22, 24 depending on the firmness of the tissue 32, as shown in FIG. 3.

Figure 4:
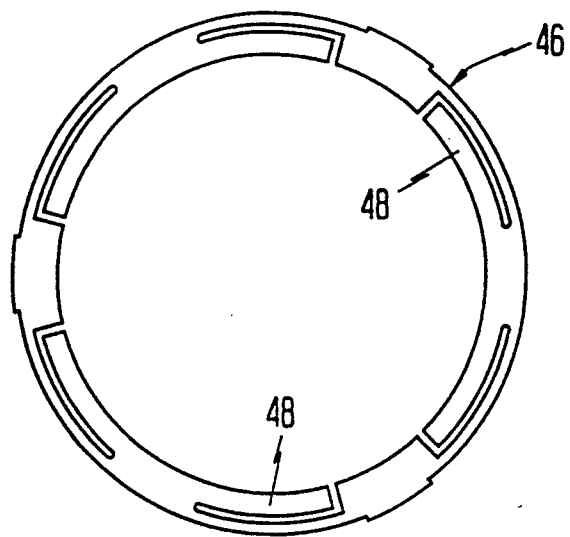
Figure 5:
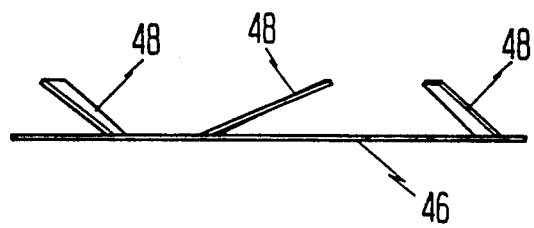

The adapter 12 includes a pot-shaped housing 34 and is arranged inside of the circular-shaped opening 36 of the holding ring 10. The housing 34 in the present exemplary embodiment consists of an essentially cylindrical wall 38 with a radially outwardly directed flange 40, on which is formed an annular contact surface 42 facing the patient. The flange 40 of the housing wall 38 in the radial direction overlaps an inwardly directed annular flange 44 of the holding ring 10. A spring ring 46, illustrated in FIGS. 4 and 5, lies between the two flanges 44 and 40. It consists of a ring of spring sheet material from which spring tongues 48 extending in the circumferential direction are stamped and which, according to FIG. 5, are bent slantingly out of the plane of the ring. In the present example, there are six such spring tongues onto which the flange 44 of the adapter housing 34 rests. As will be recognized, the adapter 12 therefore can move relative to the holding ring 10 in the direction of the axis 26 as well as wobble about the axis 26, so that it engages the skin under a pre-load determined by the spring ring 46 and can suit itself to the shape of the body section lying within the holding ring 10. It will also be recognized that the pressure, at which the adapter 12 is pressed against the upper surface of the skin 30, is practically independent of the pressure at which the holding ring 10 is pressed against the body by means of the straps 22 and 24.

The adapter housing 34 further includes a cover 50 which, for example, can be made of plastic and which, by means of a radially inwardly directed annular rib 52, can be snapped over a corresponding radially outwardly directed annular rib 54 on the housing wall 38. The cover 50 is thereby indeed held axially to the housing wall yet can nevertheless be rotated relative to the housing wall about the axis 26.

An electrode carrier, indicated generally at 56, is held inside of the cup-shaped housing 34 and is guided by a cylindrical outer wall 58, an inner wall 60 of the housing wall 38.

Between a step surface 62 of the housing wall 38 facing the housing cover 50, forming the bottom of the housing, and an abutment surface 64 lying opposite to it and on an outwardly directed flange 66 of the electrode carrier 56 is arranged a ring spring 68 which urges the electrode carrier 56 in the direction toward the cover 50 and creates an electrically conducting connection between the engagement surface 42 and the measuring circuit 84.

On the rear side of the electrode carrier 56 facing the cover 50, ramp surfaces 70 are formed which run in the circular direction and on which cams 72 on the inner side of the cover 50 slide. By a rotation of the cover 50, the cams 72 in combination with the ramp surfaces 70 press the electrode carrier 56 more or less further forwardly against the pre-load of the annular spring 68, so that the electrode carrier 56 can be adjusted in the axial direction relative to the adapter housing 34.

On the forward side of the electrode carrier 56 facing the patient's body is a concave inwardly arched carrier surface 74 on which are arranged two annular and preferably similarly surfaced electrodes 76, 78 concentric to the axis 26. In the center of the carrier surface 74 is an elevation 80 with an axis normal end surface 82. This elevation is effectively a spacer which assures that the tissue 32 which bows into the adapter housing 34 is held at a distance from the carrier surface 74, so that the skin 30 does not rest on the electrodes 76 and 78. The axial spacing of the end surface 82 from the carrier surface 74, that is the relative height of the elevation 80 above the carrier surface 74, depends on the effective diameter of the carrier surface and the effective diameter of the elevation 80. In the case where the carrier surface 74 has an effective diameter of about 45 mm, and the elevation has a diameter of 15 mm it has been found to be practical if the axial height of the elevation is between about 1.3 to 2.2 mm, or preferably 1.7 mm.

Figure 6:
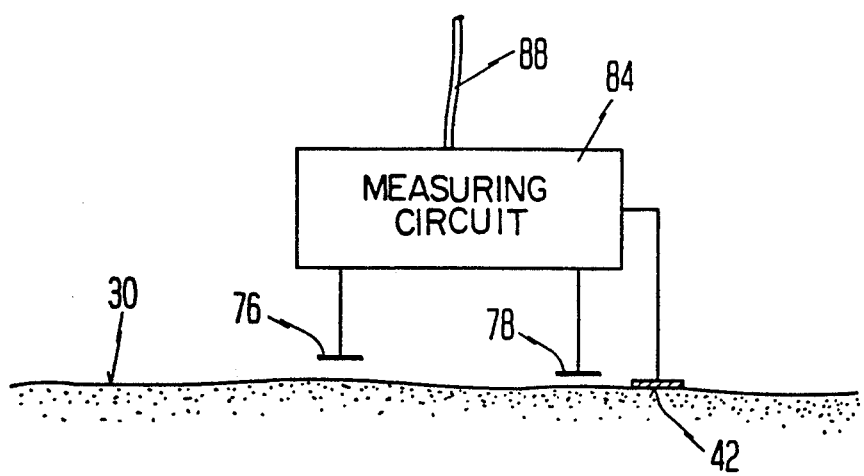

The electrodes 76 and 78 are connected with a measuring circuit 84 arranged in a rearward recess 86 in the electrode carrier 56. The electrodes 76 and 78 each form a condenser with the skin 30 which is part of an oscillator. The electrical connection of the measuring circuit 84 and the skin 30 takes place through the metallic housing wall 38 and the annular spring 68, as is schematically illustrated in FIG. 6. With a movement of the skin, such as can be evoked by a heart wall movement, the capacities of the condensers change, so that the frequency of the oscillator is likewise changed. From the resulting frequency modulation of the oscillator frequency a measurement signal can be derived. The measurement signal can be transmitted from the measuring circuit 84 to a non-illustrated indicator unit over a conductor 88 extending from the measuring head.

Figure 7:
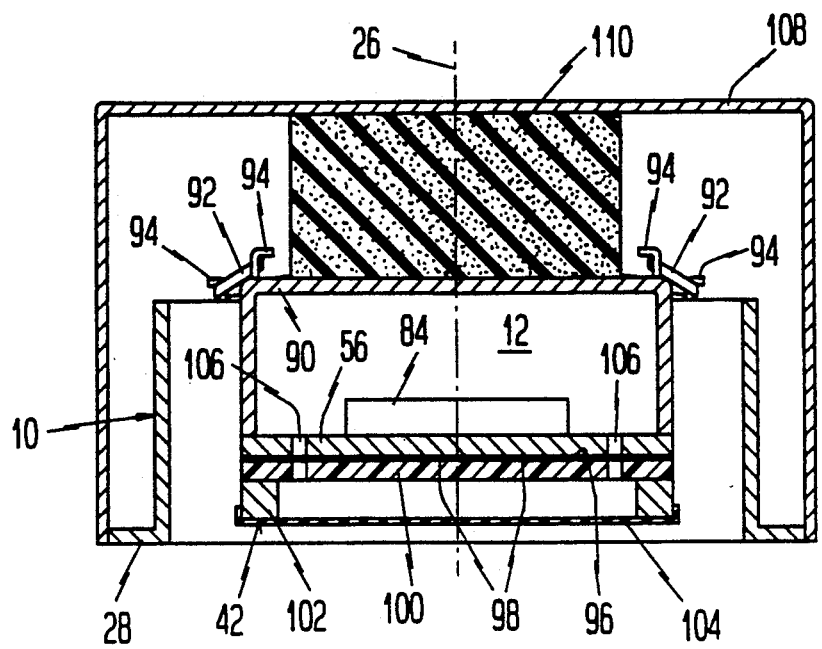

A further exemplary embodiment of the invention is illustrated in FIG. 7 in which similar parts have been similarly designated. In this embodiment the adapter 12 is resiliently supported, through its adapter housing 90, in the holding ring 10 by means of a rubber band 92, which is alternately held at several places on hooks 94 on the adapter 12 and on the holding ring 10. The hooks 94 are arranged along the circumference of the adapter housing 90 and of the holding ring 10 and are displaced from one another by similar spacings, with the rubber band 92 being slung over the hooks 94. With this type of resilient support the adapter 12 is fully cardonically suspended in the holding ring 10.

The electrode carrier 56 of the adapter 12 has a flat electrode carrier surface 96 provided with two semicircular electrodes 98. A disk 100 of plastic is provided as a spacing element which creates a basic spacing of about 1.5 mm between the skin and the electrodes 98, when the skin of a person to be examined presses against the disk 100. In this way, it is assured that even when the disk 100 partially lies on the skin, the movement of the skin is registered as a capacity change through the electrodes 98.

The perpendicular spacing between the contact surface 42 and the electrode carrying surface 96 is further determined by an annular element 102 which is arranged on the edge of the electrode carrier surface 96. For suiting different skin and tissue properties of the persons to be examined, the annular element can have different heights, for example 1.5, 2.5 or 3.5 mm, and can be made as exchangeable parts. The opening of the annular element 102 pointing toward the body is covered with an elastic protective cap 104 which, for example, is made of a rubber-like plastic material. This protective cap 104 fulfills hygienic purposes and can easily be exchanged for another. Further, this protective cap improves the long term stability of the spacing between the skin and the electrode carrier surface 96.

The space formed between the protective cap 104, the annular element 102 and the disk 100 is connected with the ambient space through two air vents 106, so that this space upon change of its volume as a result of a bulging of the protective cap 104 can either take in air or discharge air.

The holding ring 10 carries a housing cap 108. Between this housing cap 108 and the adapter housing 90 is arranged a foam rubber insert 110 which dampens the vibration of the adapter 12. The housing cap 108 is so formed that it presses the holding ring 10 against the skin by means of a wide rubber band (not illustrated) placed over the housing cap 108. This rubber band is preferably an endless band which embraces the body or person at breast level.

The measuring circuit 84 is arranged on the side of the electrode carrier 56 facing away from the body of the examined person. Preferably the electrode carrier consists of conductor board material provided with conductor paths on its rear side and which carries the electrical components of the measuring circuit. The ground potential of the measuring circuit 84 is conducted to the annular surface 28 of the holding ring by a conductor (not illustrated).

The embodiment according to FIG. 7 has the advantage that, because of the suspension by means of a rubber band 92, it is movable with very little friction and requires no depth adjustment. Because of the flat electrode carrying surface 96, it has a simple construction and can be economically made.

Figure 8:
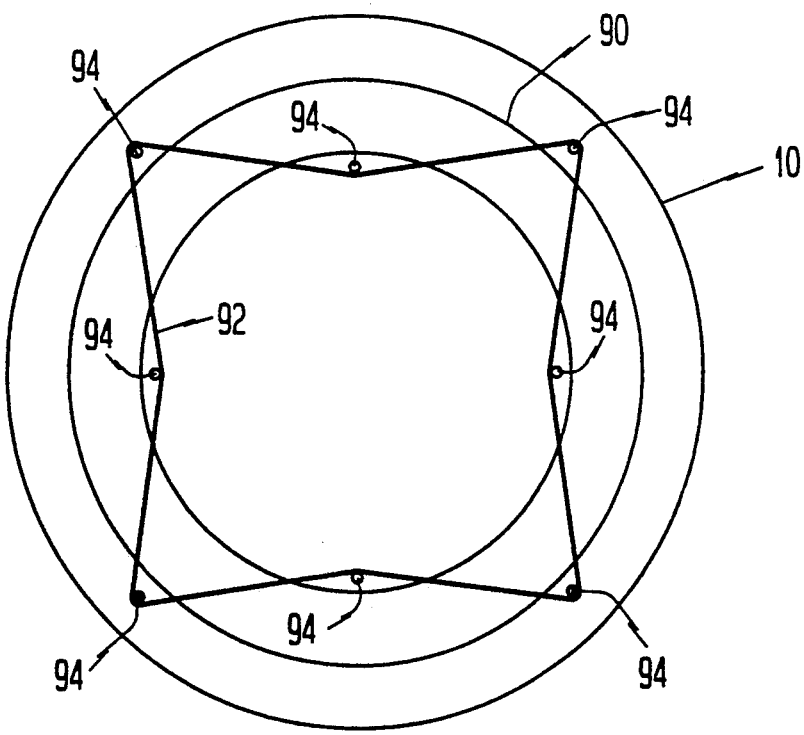

FIG. 8 shows a schematic plan view of the suspension by means of the rubber band 92 in the embodiment of FIG. 7. The rubber band 92 is led in the shape of a star over the hooks 94 of the holding ring 10 and of the adapter housing 90. The hooks 94 are arranged so as to be displaced relative to one another by equal spacings along the circumference of the holding ring 10 and of the adapter housing 90, respectively. In place of the rubber band 92, an elongated spiral spring can also be used.

It is still to be noted that different features of the embodiment of FIG. 7, such as, for example, the semicircular-shaped electrodes 98, the type of suspension by means of rubber bands 92, the dampening means in the form of foam rubber inserts 110 or the elastic protective cap 104 can also be used with the embodiment of FIG. 3.

We claim:

1. An apparatus for measuring the heart wall movement of a person, including a measuring head (10, 12) placeable onto the breast, said measuring head having an electrode arrangement (76, 78, 98) and a measuring circuit (84) for capacitively measuring skin movement with respect to the electrode arrangement (76, 78, 98), characterized in that the measuring head includes a holding ring (10) with a ring axis (26), the holding ring having an annular surface (28) perpendicular to the ring axis (26) adapted for engagement with a body (30, 32) and means (22, 28) for fastening the measuring head (10, 12) to the body, the electrode arrangement (76, 78, 98) being provided in an adapter (12) which is resiliently movably supported in and with respect to the holding ring (10) electrode arrangement being positioned enabling movement in the direction of the ring axis (26) as well as about two axes perpendicular to the ring axis, said two axes being perpendicular to one another, the adapter (12) having an annular contact surface (42) intended to engage the body and an electrode carrier (56) surrounded by the contact surface (42), and at least one electrode (76, 78, 98) carrying surface (74, 96), the electrode carrying surface (74, 96) being spaced perpendicularly from the contact surface (42) and being provided with a spacing element (80, 100).

2. An apparatus according to claim 1 further characterized in that the electrode carrying surface (74) is concave and said spacing element has an elevation (80) in a center thereof with the electrodes (76, 78) being arranged in annularly shaped sections of the electrode carrying surface between the contact surface (42) and the elevation (80).

3. An apparatus according to claim 1 further characterized in that the electrode carrier (56) is adjustable relative to the contact surface (42) in the direction of the ring axis (26).

4. An apparatus according to claim 3 further characterized in that the adapter (12) has a housing (34), the electrode carrier (56) being pretensioned by spring means (68) in a direction toward a bottom (50) of the housing, and an adjustment device (70, 72) causing movement of the electrode carrier away from the bottom of the housing.

5. An apparatus according to claim 4 further characterized by the bottom (50) of the housing being rotatable relative to a housing wall (38) about the ring axis (26), and an inner side of the bottom of the housing carrying at least one can (72) which cooperates with a control surface (70) on the electrode carrier (56) which is inclined with respect to an axis normal plane.

6. An apparatus according to claim 1 further characterized in that the adapter (12) has a pot-shaped housing (34) having an opening edge, the contact surface (42) being formed on the opening edge, and the electrode carrier (56) together with the measuring circuit (84) being arranged in the housing.

7. An apparatus according to claim 1 further characterized in that the annular contact surface (42) of the adapter (12) is electrically conducting and carries the ground potential of the measuring circuit (84).

8. An apparatus according to claim 1 further characterized in that the electrode carrying surface (96) is flat and is provided with a disk (100) as said spacing element.

9. An apparatus according to claim 8 further characterized in that the electrode carrying surface (96) is circular and carries a ring element (102) of pre-given height which is formed as an exchangeable part.

10. An apparatus according to claim 9 further characterized in that the ring element (102) has an opening directed toward the body, the opening being covered with an elastic protective cap (104).

11. An apparatus according to claim 10 further characterized in that a space is formed between the protective cap (104) and the ring element (102), the disk (100) having at least one air vent opening (106) to the atmosphere surrounding the apparatus.

12. An apparatus according to claim 1 further characterized in that the adapter (12) is resiliently supported in the holding ring (10) by spring means (48, 68, 92).

13. An apparatus according to claim 12 further characterized in that the adapter is resiliently supported in the holding ring (10) by means of at least one rubber band (92) which rubber band is alternatingly held at several places by the adapter (12) and the holding ring (10).

14. An apparatus according to claim 1 further characterized in that the holding ring (10) carries a housing cap (108).

15. An apparatus according to claim 14 further characterized in that between the adapter (12) and the housing cap (108) is arranged a resilient dampening means in the form of a foam rubber insert (110).

16. An apparatus according to claim 14 further characterized in that the housing cap (108) is round and is held between the skin and an elastic band.

17. An apparatus according to claim 1 further characterized in that the measuring circuit (84) is arranged on a side of the electrode carrier (56) facing away from the body, the electrode carrier consisting of conductor board material.

18. An apparatus according to claim 1 further characterized in that the holding ring has a surface (28) engageable with the body, the ring surface (28) being electrically conducting and carrying ground potential.

19. An apparatus according to claim 1 further characterized in that the electrode arrangement (76, 78, 98) is annular, the electrode arrangement concentrically surrounding the spacing element.

20. An apparatus according to claim 1 further characterized in that two electrodes (76, 78, 98) are arranged on the electrode carrying surface (74, 96), an oscillator of the measuring circuit (84) being associated with each of said two electrodes, the measuring circuit evaluating frequency change of the oscillators upon a change of capacity of a condenser formed between each of plural electrodes of the electrode arrangement (76, 78, 98) and the skin.

21. An apparatus according to claim 20 further characterized in that the electrodes (76, 78) are arranged concentrically to one another on the electrode carrying surface (74).

22. An apparatus according to claim 20 further characterized in that the electrode (98) are semicircular.

23. An apparatus according to claim 1 further characterized in that two electrodes (76, 78, 98) are arranged relative to one another on the electrode carrying surface (74, 96) which electrodes are connected to an oscillator of the measuring circuit so that each individual capacity determines duration of one half wave of an output signal.

24. An apparatus according to claim 1 further characterized in that the holding ring (10) is connected to fastening straps (22, 24).

* * * * *